United States Patent [19]

Bhattacharya et al.

[11] Patent Number: 5,508,451
[45] Date of Patent: Apr. 16, 1996

[54] PROCESS FOR THE PREPARATION OF DIALKALI METAL CROMOGLYCATES

[75] Inventors: Apurba Bhattacharya; Boyd A. Keys, both of Corpus Christi, Tex.

[73] Assignee: Hoechst Celanese Corporation, Sommerville, N.J.

[21] Appl. No.: 271,804

[22] Filed: Jul. 7, 1994

[51] Int. Cl.$^6$ .................................................. C07D 311/24
[52] U.S. Cl. ............................................................ 549/402
[58] Field of Search ............................................. 549/402

[56] References Cited

U.S. PATENT DOCUMENTS 3,419,578  12/1968  Fitzmaurice et al. .................... 549/402

*Primary Examiner*—Nicky Chan
*Attorney, Agent, or Firm*—James J. Mullen; Donald R. Cassady

[57] ABSTRACT

A process for preparing a dialkali metal cromoglycate which comprises (1) condensing a hydroxy substituted ketone with a condensing agent in the presence of a base material and an organic solvent; (2) subjecting the condensed material to ring-closure conditions, first in the presence of an alkali metal alkoxide and a suitable organic solvent, then followed by the addition of substantially dry mineral acid and a suitable organic solvent; and (3) hydrolyzing the ring-closed material in the presence of a base material and a suitable organic solvent to form said cromoglycate.

7 Claims, No Drawings

PROCESS FOR THE PREPARATION OF DIALKALI METAL CROMOGLYCATES

BACKGROUND OF THE INVENTION

Field of the Invention

The present invention relates to an improved process for preparing dialkali metal cromoglycates such as disodium cromoglycate.

Description of the Prior Art

The following prior art references are disclosed in accordance with the terms of 37 CFR 1.56, 1.97, and 1.98.

U.S. Pat. No. 3,419,578 (issued Dec. 31, 1968) discloses new bis-chromonyl compounds and processes for preparing the same. These compounds are useful as inhibitors of certain antigen-antibody reactions, being particularly useful for the relief and prophylaxis of asthma.

J. Indian Chem. Soc., Vol. LXIII, June 1986, pp. 600–602 discloses the synthesis of 2-carbomethoxy- and 2-(2-benzimidazolyl)chromones.

All of the above-cited prior art and any other references mentioned herein are incorporated herein by reference in their entirety.

SUMMARY OF THE INVENTION

The present invention provides an improved process for preparing a dialkali metal cromoglycate which comprises (1) condensing a hydroxy substituted ketone with a condensing agent in the presence of a base material and an organic solvent; (2) subjecting the condensed material to ring-closure conditions first in the presence of an alkali metal alkoxide and a suitable organic solvent, and then followed by the addition of substantially dry mineral acid and a suitable organic solvent; and (3) hydrolyzing the ring-closed material in the presence of a base material and a suitable organic solvent to form said cromoglycate. One of the unique features is the fact that this process can be accomplished in a single reaction vessel.

DETAILED DESCRIPTION OF THE INVENTION

One of the problems with the prior art process (as exemplified by U.S. Pat. No. 3,419,578) is the use of benzene/ether which is not environmentally friendly. When not using this mixture, the process does not work. Thus, in the processes described in U.S. Pat. No. 3,419,578, the resultant product (repeating Examples 1a and 2c therein) produced is a polymeric material which is not identifiable. The other examples exhibit a low yield. Thus, there is a need for producing these compounds in a high yield and on a repeatable basis with an environmentally suitable condition.

The present invention is an improvement in a process for preparing these bischromonyl compounds, and, in particular, the dialkali metal cromoglycates.

Thus, there is provided a process for preparing a dialkali metal cromoglycate which comprises (1) condensing a hydroxy substituted ketone with a condensing agent in the presence of a base material and an organic solvent; (2) subjecting the condensed material to ting-closure conditions first in the presence of an alkali metal alkoxide and a suitable organic solvent, and then followed by the addition of substantially dry mineral acid and a suitable organic solvent; and (3) hydrolyzing the ring-closed material in the presence of a base material and a suitable organic solvent to form said cromoglycate.

While the disclosure set forth herein is directed to a three-step process, the first step, i.e. condensation of a hydroxy-substituted ketone, such as 2,6-dihydroxyacetophenone to a diketone, is known in the art as exemplified by U.S. Pat. No. 3,419,578. Such condensation step can be carded out using known condensation conditions and include, without limitation, temperatures from about 0° C. to about 100° C., pressures from sub-atmospheric to super atmospheric, and times from minutes to days. Likewise, the operation can be batch or continuous. The condensating (condensation) agent can be any material (e.g. epichlorohydrin) which will function to accomplish the desired end result. In cases where this step requires a base material, such material can be an alkali metal hydroxide such as NaOH and KOH.

In order to facilitate the reaction in the first step, it is desirable to employ a suitable organic solvent. This solvent should be inert to the reaction taking place, i.e. it must not interfere with the condensation. Suitable solvents are aliphatic, cycloaliphatic, aromatic hydrocarbons, ether, alcohols, and mixtures thereof. In many cases, cyclic ethers and/or aliphatic alcohols have particularly proven their worth. Solvents include polar liquids which include lower alkanols including cycloalkanols, e.g., those having from one to eight carbon atoms, such as methanol, ethanol, isopropanol, butanol, pentanol, cyclohexanol, and cyclobutanol, as well as polar asymmetrically halogenated hydrocarbons, e.g., those having from one to eight carbon atoms, such as chloroform, trifluorotrichloroethane, and trichlorofluoromethane, and mixtures of the above. Aliphatic alcohols having from one to six carbon atoms are desirable. Methanol, ethanol, propanol, i-propanol, n-butanol, and/or i-butanol have proven particularly successful. In view of their good solubility in water, methanol, ethanol, and/or propanols are recommended. Methanol and/or ethanol and/or isopropanol have been found to be most suitable.

In the second step, i.e., the ring-closure, the condensed material formed in the first step, i.e., the diketone material, is subjected to ring-closure conditions and which contain a two-stage addition of materials, whereby the overall result is the formation of the ester form of the cromoglycate. Any ring-closing agent can be used as long as it accomplishes the desired end result, i.e., transformation of the "condensed" ketone (diketone material) to the cromoglycate. Such ring-closing agents include, without limitation, any diester of oxalic acid such as diethyl oxalate. This two-stage addition of materials is one of the critical features of the instant invention. It was also found that if only, for example, sodium ethoxide/ethanol is used (i.e. there is no second stage addition) it promotes the reverse reaction (i.e. the partial ring opening of the cromoglycate to the diketone material). So, at the end of the reaction, there is a statistical mixture of one-ring-closed and one-ring-opened products. This gives rise to cumbersome purification problems.

In the first stage of the second step, and generally after the diketone material and the ring-closing agent are charged into a solution vessel, there is added a suitable organic solvent and an alkali metal alkoxide. The organic solvent is the same as that solvent employed in the first step described above. The amount of solvent employed is from about 10% to about 500% by weight, based on the combined weight of the diketone and the ring-closing agent.

The amount of solvent is not critical but should be sufficient to facilitate the overall reaction. The alkali metal alkoxide is from the group comprising sodium ethoxide and potassium ethoxide.

The alkali metal alkoxide is used in an amount of from about 10% to about 100% by weight, based on the combined weight of the diketone and the ring-closing agent.

After the first stage addition, the mixture is heated to a temperature of from about 0° C. to about 100° C., preferably from about 30° C. to about 90° C., for a sufficient period of time to effect conversion of the reactants.

During the second stage addition, a substantially dry mineral, i.e. a mineral acid having a water content less than about 2% by weight, acid and a suitable organic solvent are added to the reaction mixture formed after the first stage addition. The mineral acid is from the group HCl and $H_2SO_4$. The amount of mineral acid utilized is from about 20% to about 100% by weight based on the total or combined weight of the diketone and the ring-closing agent. The organic solvent is the same as disclosed above and used in the same amounts. After the second stage addition is completed, the overall reaction mixture can be heated in a similar manner as applied to the first stage addition. Likewise, during both of the stage additions, mixing can be employed to facilitate the reaction.

The sequence of addition of the first stage and the second stage is critical and cannot be reversed; otherwise the benefits of the instant invention are not achieved.

At the end of the second stage addition, and after heating thereof, the product is isolated from the reaction mixture. However, before the isolation, it may be desirable to contact the overall reaction mixture or mass with an organic amine such as triethylamine in order to facilitate a better recovery of the diester of the cromoglycate. For example, it is desirable to isolate the cromoglycate ester (i.e. the product) from the reaction mixture after the two-stage additions. The product is insoluble in the reaction mixture and it can be quenched in water for separation purposes. However, the mineral acid present in the reaction mixture needs to be neutralized before the quenching takes place in order to prevent the partial hydrolysis of the ester moiety. Typical neutralization agents such as NaOH and $Na_2CO_3$ could be used but this complicates the isolation since additional salts are formed. Organic amines, such as triethylamine, have been found suitable to use as the neutralization agent since the salts formed are also soluble in both the ethanol solvent and in water and thus the insoluble product can be separated after the water quench when followed by filtration.

The third step in the present invention process is the hydrolysis of the diester of the cromoglycate to the desired salt of the cromoglycate. This third step is also critical in that the hydrolysis is conducted under mild basic conditions via employing, in addition to an organic solvent, a base material, such as NaOH or KOH, which has a molar concentration of from about 0.01 to about 1.5. It is critical in this third step that the basic conditions be mild in order to form the salt material. If the base material is used in concentrations of about 2.0 molar or greater or refluxed at an elevated temperature as mentioned in U.S. Pat. No. 3,419,578, it has been found that the salt material will not be formed but that the diester material will undergo a "ring-opening" to produce the diketone material. The organic solvent in this third step is the same as the material described above and used in the same amounts. The hydrolysis is generally conducted at a temperature of less than about 50° C., preferably less than about 30° C.

The following Scheme I represents a flow sheet of the three-step process set forth above, and specifically, the preparation of disodium cromoglycate from a ketone such as 2,6-dihydroxy-acetophenone.

SCHEME I
SYNTHESIS OF DISODIUM CROMOGLYCATE

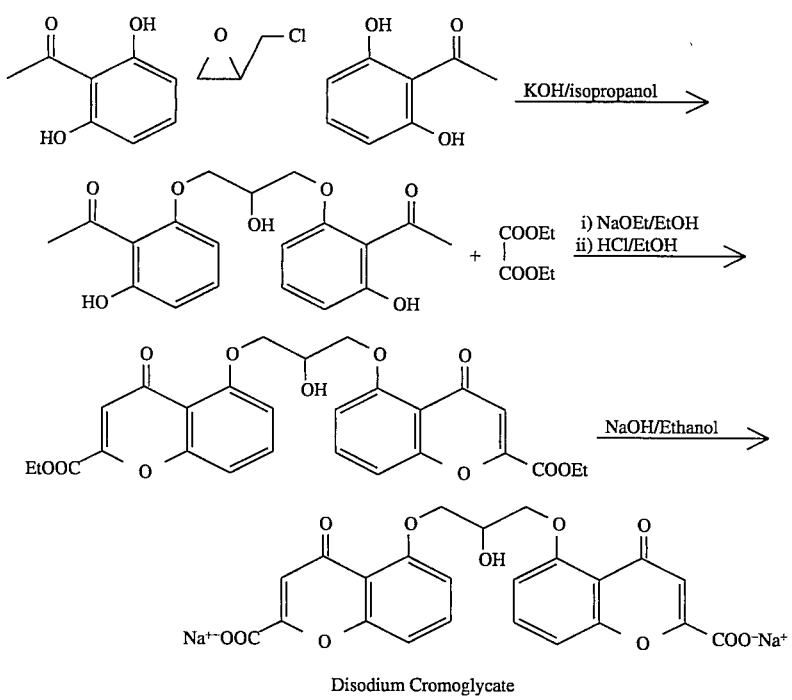

Disodium Cromoglycate

While the above Scheme I is directed to the preparation of disodium cromoglycate, it is to be understood that other bis-chromonyl compounds. (such as those disclosed in U.S. Pat. No. 3,419,578) can be prepared by the improved process of the present invention. Thus, these bis-chromonyl compounds can be prepared by a process which comprises the steps of (a) subjecting a diketone compound to ring-closure conditions first in the presence of an alkali metal alkoxide and a suitable organic solvent and then followed by the addition of substantially dry mineral acid and a suitable organic solvent to form a diester of the bis-chromonyl compound; and (b) hydrolyzing the diester of the bis-chromonyl compound in the presence of a base material and a suitable organic solvent to form the salt form of the bis-chromonyl compound.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1 (Comparative)

Example 2(c), which uses Example 1(b), of U.S. Pat. No. 3,419,578 is repeated as follows:

In a 250 ml round bottom flask equipped with a magnetic stirrer and condenser, there is charged 7.26 grams (20 mM) 1,3-bis(2-acetyl-3-hydroxyphenoxy)- 2-hydroxy propane, 15 milliliters diethyl oxalate, 30 milliliters ethanol, and 50 milliliters toluene. The mixture is stirred at room temperature (approximately 20° C.) for several minutes. To this mixture, there is slowly added three grams (130 mM) sodium pellets. Approximately halfway through the sodium pellet addition the temperature increases to 73° C. The addition is stopped and the mixture is allowed to cool. The addition of the second half of the sodium pellets is then completed; the temperature does not increase during the second addition. After the entire sodium pellet addition, the mixture is heated to its reflux temperature (approximately 73° C.) for twenty hours. After twenty hours, no starting material remains as determined by HPLC. The mixture is cooled to room temperature (approximately 20° C.), then quenched in methylene chloride and a 1M HCl solution. The two phases are separated and the organic phase is passed through a small bed of silica gel to remove any original material. The resultant filtrate is concentrated in a rotovap to produce an oil. This oil would not crystallize in small test tubes using different solvents. The oil is submitted for NMR analysis and the results thereof show that no desired product, i.e. the cromoglycate) is found. Basically, the result is a polymeric material with numerous NMR peaks.

EXAMPLE 2

Preparation of Disodium Cromoglycate

Into a 250 ml round bottom flask equipped with a magnetic stirrer, reflux condenser, and a nitrogen inlet, there is charged 6.54 grams (18 mM) 1,3-bis(2-acetyl- 3-hydroxyphenoxy)-2-hydroxypropane, 14.4 grams (96 mM)/13.5 ml diethyl oxylate and 60 ml ethanol. The materials are stirred at room temperature for three minutes. At the end of this mixing, 8.25 (119.1 mM) sodium ethoxide is added. The sodium ethoxide solids clump together but soon dissolve after heating the overall mixture to reflux (approximately 85° C.). After twenty hours, HPLC analysis confirms the 100% conversion of the reactants. The mixture is then cooled to room temperature (approximately 20° C). An HCl/ethanol solution is prepared by dissolving 14.31 grams HCl gas into 40.13 grams ethanol. Approximately34.2 grams HCL/ethanol solution is added via addition funnel at room temperature. Initially the mixture becomes thick with the HCl/ethanol addition, but this thins over time. After cooling and slowly re-heating to reflux, the mixture is thinner and stirs well. The mixture is then refluxed for thirty minutes then cooled to 30° C. The mixture is then added via dropper to a solution of 15.5 grams (154 mM) triethylamine in 240 ml water at 40° C. The overall mixture (40° C.) is then filtered through a 350 ml medium glass fritted funnel. The brown solids remaining in the funnel are washed with two bed volumes of hot water. The wet solids are placed in an open vacuum and allowed to dry; recovery is 8.22 grams of solids which, analyzed by NMR, is 1,3-bis(2-carboxy-chromen-5-yloxy)-2-hydroxypropane. Theoretical yield is 9.44 grams and thus gives a percent yield of 88.1%.

The preceding represents the second step of the instant invention. The third step is conducted as follows:

Into a 250 ml round bottom flask equipped with a magnetic stirrer and addition funnel, there is added 10.01 grams 1,3-bis(2-carboxychromon-5-yloxy)-2-hydroxypropane (prepared in the manner described above) and 50 ml ethanol. The tan-colored mixture is stirred for three minutes at room temperature (approximately 20° C.). There is slowly added 38.1 ml 1N NaOH via addition funnel. The resultant mixture thickens upon addition but remains fluid enough to stir. After the addition is complete, HPLC analysis indicates 100% conversion of the reactants. There is added 50 ml ethanol to the tan-colored mixture and this is stirred for thirty minutes at room temperature (approximately 20° C.). The overall mixture is filtered through a course glass fritted funnel and the resultant solids are washed with 3-4 bed volumes (200 ml) 95% ethanol/5% water mixture. The wet solids are placed in a vacuum oven (50° C., nitrogen atmosphere) and dried. The yield is 9.1 grams; theoretical yield is 9.74 grams. The yield is 93% of cromolyn sodium (disodium chromoglycate) and which has the formula as shown in Scheme I above.

Using the inventive concepts of the present invention outlined herein, it is also within the scope of the present invention to prepare chromone-2-carboxylic acids and derivatives thereof; these "chromones" are fully described in the above-cited *J. Indian Chem. Soc.* article. For example, 2-hydroxyacetophenone can be subjected to the same procedure as set forth in Example 2 above, and the resultant material will be the sodium salt of chromone-2-carboxylic acid.

While the invention is described with respect to specific embodiments, modification thereof can be made by one skilled in the art without departing from the spirit of the invention. The details of said embodiments are not to be construed as a limitation, except to the extent indicated in the following claims.

What is claimed is:

1. A process for preparing an alkali metal cromoglycate which comprises the steps of:
   a. condensing 2,6-dihydroxyacetophenone with a condensing agent in the presence of a base material and an organic solvent under suitable condensation conditions to form 1,3-bis(2-acetyl-3-hydroxyphenoxy)-2-hydroxypropane;
   b. subjecting said hydroxypropane, formed in step (a), to suitable ring-closure conditions, first in the presence of a ring closing agent, an alkali metal alkoxide and a suitable organic solvent, then followed by the addition of substantially dry mineral acid and a suitable organic solvent to form 1,3-bis(2-carboalkoxychromon-5-yloxy)-2-hydroxypropane; and c. hydrolyzing said hydroxypropane, formed in step (b), for a sufficient period of time, temperature, and pressure, under suitable hydrolysis conditions, to form said alkali metal cromoglycate.

2. The process as set forth in claim 1 wherein in step (a), the base material is an alkali metal hydroxide.

3. The process as set forth in claim 4 wherein in step (b), there is included a ring-closing agent is a diester of oxalic acid.

4. A process for preparing disodium cromoglycate which comprises the steps of:

a. reacting 2,6-dihydroxyacetophenone with epichlorohydrin in the presence of potassium hydroxide and isopropanol to form 1,3-bis(2-acetyl- 3-hydroxyphenoxy)-2-hydroxypropane;

b. reacting said hydroxypropane with diethyl oxalate, first in the presence of sodium ethoxide and ethanol, then followed by the addition of dry hydrochloric acid and ethanol to form 1,3-bis(2-carboethoxychromon-5-yloxy)-2-hydroxypropane; and c. hydrolyzing said hydroxypropane, formed in step (b), for a sufficient period of time and temperature, and in the presence of sodium hydroxide and ethanol, to form said disodium cromoglycate.

5. The process as set forth in claim 4 wherein the hydroxypropane formed in step (b) is separated from the reaction mass by contacting said reaction mass with an organic soluble amine.

6. The process as set forth in claim 4 wherein the hydrolysis is conducted at a temperature of less than about 30° C.

7. The process as set forth in claim 4 wherein the hydrolysis is conducted with sodium hydroxide which has a molar concentration of from about 0.01 to about 1.5.

* * * * *